US008530056B2

(12) United States Patent
Pilloy et al.

(10) Patent No.: US 8,530,056 B2
(45) Date of Patent: Sep. 10, 2013

(54) SUBSTRATE WITH ANTIMICROBIAL PROPERTIES

(75) Inventors: Georges Pilloy, Jumet (BE); André Hecq, Jumet (BE); Kadosa Hevesi, Jumet (BE); Nadia Jacobs, Jumet (BE)

(73) Assignee: AGC Glass Europe, Brussels (BE)

( * ) Notice: Subject to any disclaimer, the term of this patent is extended or adjusted under 35 U.S.C. 154(b) by 735 days.

(21) Appl. No.: 11/721,691

(22) PCT Filed: Dec. 16, 2005

(86) PCT No.: PCT/EP2005/056884
§ 371 (c)(1),
(2), (4) Date: Jun. 14, 2007

(87) PCT Pub. No.: WO2006/064060
PCT Pub. Date: Jun. 22, 2006

(65) Prior Publication Data

US 2009/0324990 A1 Dec. 31, 2009

(30) Foreign Application Priority Data

Dec. 16, 2004 (EP) .................................... 04106648
Mar. 10, 2005 (EP) .................................... 05101882

(51) Int. Cl.
*B32B 15/04* (2006.01)
*B32B 17/06* (2006.01)

(52) U.S. Cl.
USPC .......... 428/432; 428/689; 428/697; 428/699; 428/701; 428/702

(58) Field of Classification Search
USPC ................ 428/428, 689, 699, 701, 702, 432, 428/697
See application file for complete search history.

(56) References Cited

U.S. PATENT DOCUMENTS

| | | | | |
|---|---|---|---|---|
| 5,595,813 | A * | 1/1997 | Ogawa et al. | 428/212 |
| 6,677,063 | B2 * | 1/2004 | Finley | 428/701 |
| 7,323,249 | B2 * | 1/2008 | Athey et al. | 428/432 |
| 7,527,832 | B2 * | 5/2009 | Sakoske et al. | 427/450 |
| 7,862,910 | B2 * | 1/2011 | Krisko et al. | 428/699 |
| 2002/0114945 | A1 * | 8/2002 | Greenberg et al. | 428/336 |
| 2003/0235695 | A1 * | 12/2003 | Greenberg et al. | 428/432 |
| 2004/0131894 | A1 | 7/2004 | Erdemir et al. | |
| 2004/0166173 | A1 | 8/2004 | Albach | |
| 2005/0252108 | A1 * | 11/2005 | Sanderson et al. | 52/171.3 |
| 2009/0324990 | A1 * | 12/2009 | Pilloy et al. | 428/615 |
| 2011/0081542 | A1 * | 4/2011 | Pilloy et al. | 428/341 |

FOREIGN PATENT DOCUMENTS

| | | | |
|---|---|---|---|
| JP | 06330285 | | 11/1994 |
| JP | 11-322524 | | 11/1999 |
| WO | WO 9513704 | | 5/1995 |
| WO | WO 2005/030665 | * | 4/2005 |

OTHER PUBLICATIONS

Ryu et al., Effect of calcination on the structural and optical properties of M/TiO2 thin films by RF magnetron co-sputtering, Feb. 2004, 58, p. 582-587.*

* cited by examiner

*Primary Examiner* — David Sample
*Assistant Examiner* — Lauren Colgan
(74) *Attorney, Agent, or Firm* — Oblon, Spivak, McClelland, Maier & Neustadt, L.L.P.

(57) ABSTRACT

An antimicrobial substrate (glass, ceramic or metallic) coated on at least one of its surface with at least one mixed layer deposited by a sputtering under vacuum magnetically enhanced process is described. The layer comprising at least one antimicrobial agent mixed to binder material chosen amongst the metal oxides, oxynitrides, oxycarbides or nitrides. This substrate present antimicrobial properties, in particular bactericidal activity even when no thermal treatment has been applied. If a tempered and antimicrobial glass is required, the same co-sputtering process can be used, optionally an underlayer can be added. Antimicrobial properties are maintained even after a tempering process.

18 Claims, No Drawings

SUBSTRATE WITH ANTIMICROBIAL PROPERTIES

CROSS-REFERENCE TO RELATED APPLICATIONS

This application is the entry into the United States of PCT Application Number PCT/EP/056884 filed Dec. 16, 2005 and claims priority from European Patent Application Nos. 05101882.8 filed Mar. 10, 2005 and 04106648.1, filed Dec. 16, 2004, the entirety of each of which are hereby incorporated by reference.

BACKGROUND

The present invention relates to a substrate of any type: metal, glass, glass ceramic, wherein at least one of its surfaces has antimicrobial, in particular antibacterial or antifungal, properties. The present invention also relates to processes for the production of such a substrate.

In the field of ceramic substrates, EP 653 161, for example, describes the possibility of covering these with a glaze composed of silver to provide them with antibacterial properties.

In the field of glass-type substrates, sol-gel type processes are known to provide an antimicrobial surface. These processes require a hardening stage of the sol-gel layer, which involves elevated temperatures in the order of 500°-600° C. (sintering temperature). Processes are also known that require the substrate to be dipped in a composition comprising a silver salt. In this case, a silver layer is not deposited, but an ion exchange takes place in the solution at an elevated temperature.

A process for producing a glass substrate having antimicrobial properties is also known from EP 1449816. This process requires both a drying stage between 20° and 105° C. and a thermal treatment at 600°-650° C. This thermal treatment has some disadvantages particularly with respect to cost and uniformity of the product. Moreover, it renders the process very poorly reproducible, since it has been found that at these temperatures the diffusion of the silver is very rapid and a slight variation in the duration of the thermal treatment results in a significant variation in the depth of diffusion of the silver, and therefore this causes variation in the antibacterial properties of the substrate. It may also be noted that such a thermal treatment causes an undesirable yellow colouration of a soda-lime glass substrate. Furthermore, with this process, after having been treated, the product may no more be cut into particular size because of the necessary tempering process.

SUMMARY

Therefore, there is a need to provide a substrate, either glass or metallic, with antimicrobial properties, which is easy to use and inexpensive to produce.

DETAILED DESCRIPTION

The present invention relates to a substrate coated with at least one mineral layer, particularly selected from metal oxides, oxynitrides, oxycarbides, carbides, DLC (diamond like carbon) or nitrides, said layer comprising at least one antimicrobial agent. In particular, the mineral layer can be selected from oxides of silicon, tin, zinc, titanium, niobium, aluminium, zirconium or mixture thereof, for example ZnSnOx. Particularly preferred nitrides are silicon, titanium and aluminium nitrides and mixture thereof.

The antimicrobial agent can be selected from various inorganic agents known for their antimicrobial properties, in particular silver, copper and zinc. Advantageously, the antimicrobial agent is in metallic form.

The substrate can be metallic, e.g. made of steel, or stainless steel or ceramic type or plastic or thermoplastic type substrate or a glass-type substrate, in particular a sheet of flat glass, particularly soda-lime glass which may be float glass. It may be clear glass or coloured glass. It may comprise a reflective layer (to form a mirror) or a layer of enamel or painting (for wall covering), generally at the surface opposite to the antimicrobial surface.

The substrate may have a thickness within the range of 2.5 to 12 mm.

The substrate may have a surface area of greater than 0.8 m to 0.8 m; it may be adapted to be cut to a finished size by a subsequent cutting operation.

In some embodiments of the invention, a substrate having antimicrobial agents present at at least one exposed surface may be an annealed sheet of glass. The term annealed sheet of glass is used herein to mean that the glass may be cut to size without breaking in the way that a tempered or hardened sheet of glass would break upon cutting. Such an annealed sheet of glass preferably has a surface compression of less than 5 MPa.

It has been found that it is possible to cause antimicrobial agents to diffuse into a mineral coating formed from one or more layers of metal oxides, oxynitrides, oxycarbides or nitrides, when this coating has been firstly deposited on a substrate of whatever type. The diffusion of the antimicrobial agent can also occur in a topcoat deposited above the layer containing the antimicrobial agent.

For example, the substrate can be coated with a first layer that blocks or slows down the diffusion of the antimicrobial agents and optionally with a second layer serving as a reservoir for the antimicrobial agents. Those functions can be ascertained on a product made according to the invention by comparing the antimicrobial effect of similar products with and without undercoating and/or by analysing diffusion profiles.

Each layers of the undercoat may in particular have a thickness comprised between 1 and 1000 nm, preferably between 1.5 and 800 nm, most preferably between 2 and 600 nm.

In particular, the blocking underlayer is chosen amongst pyrolitic and sputtered layers, in particular layers comprising metal oxide, metal or metal alloy compound, such as Pd, Ni—Cr, TiOx, NiCrOx, Nb, Ta, Al, Zr or ZnAl, or mixture thereof.

In the case of a glass substrate, it is conceivable that the antimicrobial glass substrate thus obtained is subjected to a thermal treatment stage such as thermal tempering, bending or hardening, while still retaining its antimicrobial properties.

In the case of metallic substrate, particularly preferred undercoat and/or mixed layers are chosen amongst titanium oxide, titanium nitride or zirconium oxide.

The substrate according to the invention preferably has an antibacterial effect on a large number of bacteria, whether gram positive or gram negative bacteria, in particular on at least one of the following bacteria: *Escherichia coli, Staphylococcus aureus, Pseudomonas aeruginosa, Enterococcus hirae*. The antibacterial effect measured in accordance with the standard JIS Z 2801 is in particular, at least on any one of these bacteria, higher than log 1, preferably higher than log 2 and particularly preferred higher than log 2.5. The substrate will be considered bactericidal according to the standard JIS Z 2810 if it has an effect higher than log 2. However, the invention also relates to substrates that have a lesser effect (for example bacteriostatic effect, which means that the bacteria are not necessarily killed but can not developed any more).

The substrate according to the invention advantageously has an antifungal (fungicidal or fungistatic) effect on at least one fungus, in particular *Candida albicans* or *Aspeius nier.*

It has been found that it is possible to deposit the mineral layer and the antimicrobial agent in one single step over the entire substrate, whether it is made of metal, e.g. steel, or is a glass-type substrate. In particular, with the dassic method of magnetron sputtering, it is possible to form a layer, e.g. of a metal oxide doped with an antimicrobial agent, e.g. silver, using two metal targets in the same deposition chamber (co-sputtering) or using a sole target with mixed metal. With this process no additional or subsequent diffusion of the antimicrobial agent may be needed. We obtain a antimicrobial substrate in one step, without any thermal treatment which is cost saving.

It has also been discovered that, if a tempered and antimicrobial glass is required, the same process may be used, and optionally an underlayer may be added. Antimicrobial (in particular bactericidal but also bacteriostatic) properties may be maintained even after a tempering process (implying high temperature treatment during perhaps 5 to 10 min).

Layers of Ag doped metal oxide deposited in a single step by co-sputtering, wherein the concentration of Ag can vary from 0.1 to 5%, have been made which have antimicrobial properties with a simple process which does not require any thermal treatment.

When the substrate used is a clear glass, it can advantageously have antimicrobial properties as well as a neutral colouration in reflection. In particular, the colorimetric indexes (CIELAB system) in reflection a* and b* (Bluminant C, 10° observer) may be in the range of between −10 and 6, preferably between −5 and 3 and particularly preferred between −2 and 0, and the purity may be less than 15%, preferably less than 10% and particularly preferred less than 5%.

If the substrate is a coloured glass, antimicrobial properties may be obtained without changing very much the initial colour of the substrate. The change of coloration is generally expressed with the colorimetric index by Delta E*; DeltaE*= $[(1^*_1-1^*_2)^2+(a^*_1-a^*_2)^2+(b^*_1-b^*_2)^2]^{1/2}$. A DeltaE* lower than 3, preferably lower than 2 may be obtained for an antimicrobial substrate according to the invention.

When the glass substrate used is a clear glass, it may advantageously have both antimicrobial properties and a visible light absorption of less than 1.5%, preferably less than 1.4% and particularly preferred less than 1.3%. It may have a visible light transmission within the range of 80 to 91%, preferably 84 to 90%. And the visible light reflection may be less than 15, preferably less than 12%, most preferably less than 10%.

The substrate according to the invention preferably has in particular an antimicrobial effect after at least one of the following accelerated ageing tests: wet spray test (test over 20 days in a chamber with a humidity of more than 95% at 40° C.), after 500 hours of UV irradiation (4 340A ATLAS lamps, chamber at 60° C.), after 24 hours immersed in a solution of $H_2SO_4$ (0.1 N), after 24 hours immersed in a solution of NaOH (0.1 N).

It may be advantageous to use an undercoat comprising an oxide of zirconium This may particularly be so when the mixed layer comprises an antibacterial agent and an oxide of titanium, particularly comprising of consisting essentially of titanium oxide in its anatase crystallised form.

Additional or alternative embodiments of the present invention are described in dependant claims.

The present invention shall be described in more detail below, in a non-restrictive manner:

Example 1

Two samples of clear soda-lime glass were coated with a layer of $SiO_2$(Al):Ag by co-sputtering. Two metal targets were used in a mixed atmosphere of argon and oxygen: one was composed of silicon doped with 8% Al and the second target was a metallic silver target. The electric power supply to the layers was regulated in order to obtain 0.5 atomic % of Ag in the layer for the first sample and 1 atomic % of Ag in the layer for the second. The layer thickness was 80 nm for the first sample and 150 nm for the second.

The bactericidal and fungicidal properties (in particular on *E. Coli*) of the samples were analysed in accordance with standard JIS Z 2801. A log 1 level indicates that 90% of the bacteria inoculated onto the surface of the glass were killed in 24 hours in the conditions of the standard; log 2 indicates that 99% of the bacteria were killed; log 3 indicates that 99.9% of the bacteria deposited were killed etc.

A value of log 4.2 was obtained for both samples of example 1.

Example 2

Two samples of clear soda-lime glass were coated with a layer of $SnO_2$—Ag by co-sputtering using two metallic targets (Sn and Ag). The thickness of the layer is respectively 80 and 40 nm and the quantity of Ag deposited is respectively 2 and 30 mg/m2. The antibacterial effect was measured in the same manner as in the previous example. Values of log 4.4 and 4.5 were obtained.

Example 3

Two samples of clear soda-lime glass were coated with a layer of ZrO2-Ag by co-sputtering using two metallic targets (Zr and Ag). The electric power supply to the layers was regulated in order to obtain 1.2 atomic % of Ag for the first sample and 3.4 atomic % of Ag for the second. The antibacterial effect was measured in the same manner as in the previous examples. Values of log 4 were obtained for both samples.

Example 4

A co-sputtering of SnO2-Ag was deposited over two different substrates. The quantity of Ag deposited amounts to 46 mg/m2 of surface and the thickness of the mixed layer is 17 nm.

The first substrate is a clear soda lime glass with an double underlayer SiOx (70 nm) and SnO2:F (320 nm) deposited by Chemical Vapor Deposition. The second substrate is a clear soda lime-glass coated with a 50 nm thick SiO2 layer deposited by vacuum sputtering. Both samples were subjected to a common tempering process (670° C. during 10 min follow by quick cooling).

The antibacterial effect on *E. Coli*, measured as in the previous examples gives values of log 1.76 and 1.38. This meant a bactericid effect were between 90 and 99% of the inoculated bacteria were killed.

Example 5

A co-sputtering of SnO2-Ag was deposited over 2 different metallic substrates. The quantity of Ag deposited amounts to 46 mg/m2 of surface and the thickness of the mixed layer is 17 nm.

The first substrate is a galvanized steel of the commercial type "ST37" with a thickness of 1.5 mm. The second substrate is a sample of steel laminated under cold condition and without oil of a thickness of 0.2 mm.

The antibacterial effect on *E. Coli*, measured as in the previous examples gives values of log 3.53 for both samples.

The invention claimed is:

1. A glass substrate comprising:

an undercoating covering the substrate, said undercoating comprising a first layer based on $ZrO_2$ and a second layer based on $TiO_2$ at least partially crystallised in the anatase form;

at least one mixed layer coated on at least one surface of said substrate deposited by sputtering under (i) a vacuum process, or (ii) a magnetically enhanced vacuum process, to form a coated glass substrate, said mixed layer having antimicrobial properties and comprising from 2 to 1000 mg of at least one antimicrobial agent per $m^2$ of substrate surface and at least one binder material comprising $SnO_2$, $ZrO_2$, NbOx, oxynitrides, oxycarbides, carbides, DLC, nitrides, or mixtures thereof, and wherein the antimicrobial agent is selected from the group consisting of silver and copper.

2. The substrate according to claim 1, wherein said undercoating has a function of slowing down or blocking the diffusion of antimicrobial agents.

3. The substrate according to claim 1, wherein the mixed layer comprises tin oxide and an antimicrobial agent selected from silver and copper.

4. The substrate according to claim 1, wherein said substrate presents annealed characteristics.

5. The substrate according to claim 1, wherein the binder material is selected from the group consisting of $SnO_2$, $ZrO_2$, NbOx, $Si_3N_4$, TiN, AlN, and mixtures thereof.

6. The substrate according to claim 1, wherein on at least one of the following bacteria: *E. coli, S. aureus, P. aeruginosa* (measured in accordance with the standard JIS Z 2801), the antimicrobial agent has a bactericidal effect higher than log 1.

7. The substrate according to claim 1, wherein said substrate is able to be tempered at a later stage and in that it keeps antimicrobial properties after the treatment of tempering.

8. The substrate according to claim 7, wherein the undercoating has a function of blocking or slowing down the migration of the antimicrobial agent during tempering.

9. The substrate according to claim 1, wherein on at least one of the following bacteria: *E. coli, S. aureus, P. aeruginosa* (measured in accordance with the standard JIS Z 2801), the antimicrobial agent has a bactericidal effect higher than log 2.

10. The substrate according to claim 1, wherein on at least one of the following bacteria: *E. coli, S. aureus, P. aeruginosa* (measured in accordance with the standard JIS Z 2801), the antimicrobial agent has a bactericidal effect higher than log 2.5.

11. The substrate according to claim 1, wherein the coated glass has a light reflection (LR)<15%.

12. The substrate according to claim 1, wherein the mixed layer comprises from 10 to 250 mg/$m^2$ of antimicrobial agent per $m^2$ of substrate surface.

13. The substrate according to claim 1, wherein the mixed layer comprises from 20 to 100 mg/$m^2$ of antimicrobial agent per $m^2$ of substrate surface.

14. The substrate according to claim 1, wherein the mixed layer comprises a layer of Ag doped $SnO_2$, $ZrO_2$, NbOx, $Si_3N_4$, TiN, AlN or mixture thereof.

15. The substrate according to claim 1, wherein the mixed layer comprises a layer of Ag doped ZnSnOx.

16. The substrate according to claim 1, wherein the undercoating is between said substrate and said mixed layer and said undercoating comprises a pyrolytic layer, a sputtered layer, or both a pyrolitic layer, a sputtered layer, or both.

17. The substrate according to claim 1, wherein said mixed layer is an outermost layer of said substrate.

18. A glass substrate comprising:

an undercoating covering the substrate, said undercoating comprising a first layer based on ZrO2 and a second layer based on TiO2 at least partially crystallised in the anatase form;

at least one sputtered mixed layer coated on at least one surface of said substrate, said mixed layer having antimicrobial properties and further comprising (i) from 2 to 1000 mg of at least one antimicrobial agent per $m^2$ of substrate surface and (ii) at least one binder material comprising $ZrO_2$, NbOx, oxynitrides, oxycarbides, carbides, DLC, nitrides, or mixtures thereof.

* * * * *